United States Patent
Saito et al.

(10) Patent No.: US 8,699,015 B2
(45) Date of Patent: Apr. 15, 2014

(54) SCHEMATIC EYE AND ADJUSTMENT METHOD AND EVALUATION METHOD FOR OPTICAL COHERENCE TOMOGRAPHY APPARATUS

(75) Inventors: Kenichi Saito, Yokohama (JP); Shuichi Kobayashi, Yokohama (JP); Mitsuro Sugita, Tokyo (JP); Yasuyuki Numajiri, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 438 days.

(21) Appl. No.: 13/069,806

(22) Filed: Mar. 23, 2011

(65) Prior Publication Data

US 2011/0249236 A1 Oct. 13, 2011

(30) Foreign Application Priority Data

Apr. 13, 2010 (JP) ................................. 2010-092627
Mar. 1, 2011 (JP) ................................. 2011-044299

(51) Int. Cl.
*G01B 9/00* (2006.01)

(52) U.S. Cl.
USPC ........ 356/124; 356/497; 356/243.1; 359/449; 351/206

(58) Field of Classification Search
USPC ........... 356/124–127, 243.1–243.8, 479, 497; 351/206, 221; 600/322, 316, 328, 473
See application file for complete search history.

(56) References Cited

U.S. PATENT DOCUMENTS

| | | | |
|---|---|---|---|
| 4,772,102 A * | 9/1988 | Fergason et al. ............ | 349/86 |
| 4,830,483 A | 5/1989 | Kohayakawa et al. | |
| 4,866,243 A | 9/1989 | Sakane et al. | |
| 5,144,524 A * | 9/1992 | Tullis et al. ............ | 362/293 |
| 5,894,337 A | 4/1999 | Okinishi et al. | |
| 6,192,269 B1 | 2/2001 | Okumura et al. | |
| 6,239,907 B1 * | 5/2001 | Allen et al. ............ | 359/443 |
| 6,324,420 B1 | 11/2001 | Kishida et al. | |
| 6,337,993 B1 | 1/2002 | Kishida et al. | |
| 6,454,722 B1 | 9/2002 | Numajiri et al. | |
| 6,699,198 B2 | 3/2004 | Numajiri | |
| 6,834,202 B2 | 12/2004 | Ono | |
| 7,903,257 B2 * | 3/2011 | de Boer et al. ............ | 356/497 |
| 7,911,692 B2 * | 3/2011 | Okamoto ............ | 359/449 |
| 7,982,879 B2 * | 7/2011 | Desjardins et al. ............ | 356/477 |
| 2010/0103374 A1 | 4/2010 | Hirose et al. | |
| 2010/0166293 A1 | 7/2010 | Sugita et al. | |
| 2010/0181462 A1 | 7/2010 | Sugita | |
| 2011/0096333 A1 | 4/2011 | Suehira et al. | |
| 2011/0098560 A1 | 4/2011 | Suehira et al. | |
| 2011/0242487 A1 | 10/2011 | Yuasa et al. | |
| 2011/0279778 A1 | 11/2011 | Saito | |
| 2013/0092230 A1 * | 4/2013 | Pereira et al. ............ | 136/256 |

FOREIGN PATENT DOCUMENTS

JP 2002-165759 A 6/2002

OTHER PUBLICATIONS

Tyler S. Ralston et al., Real-time interferometric synthetic aperture microscopy, Optics Express, vol. 16, No. 4, Feb. 18, 2008, pp. 2555-2569.

* cited by examiner

*Primary Examiner* — Hoa Pham
(74) *Attorney, Agent, or Firm* — Fitzpatrick, Cella, Harper & Scinto

(57) ABSTRACT

A schematic eye is used for the evaluation of the optical system of an optical coherence tomography apparatus which captures a tomogram of the fundus. The eye includes a first optical member which irradiated light from the optical system strikes and a second optical member which irradiated light from the first optical member strikes. A plurality of layers having different scattering intensities in the incident direction of irradiated light are formed on the second optical member.

13 Claims, 9 Drawing Sheets

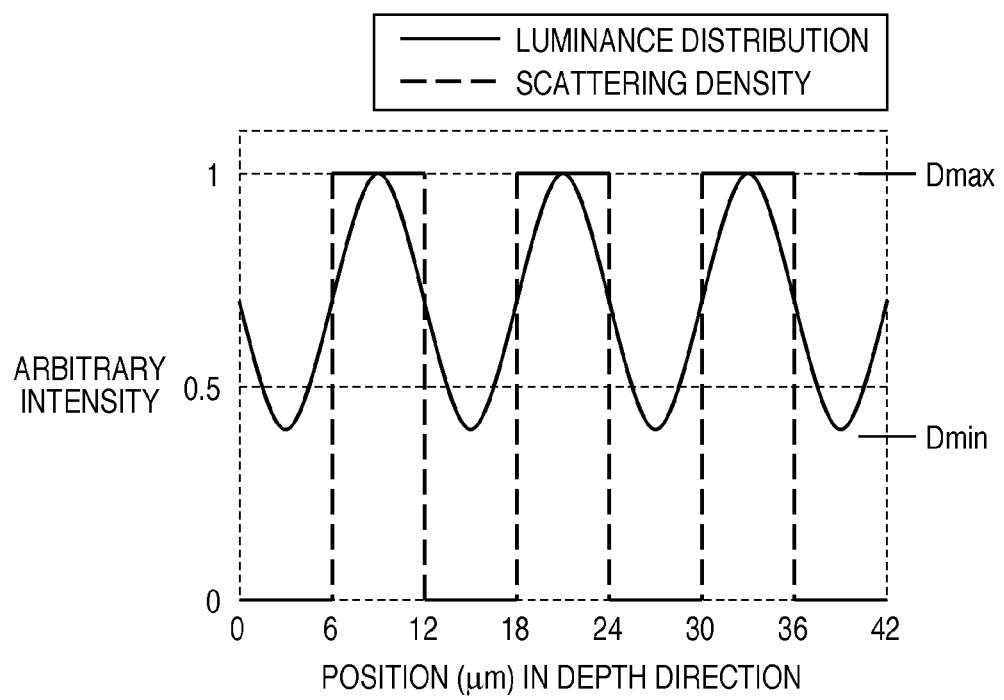
F I G. 3

F I G. 10
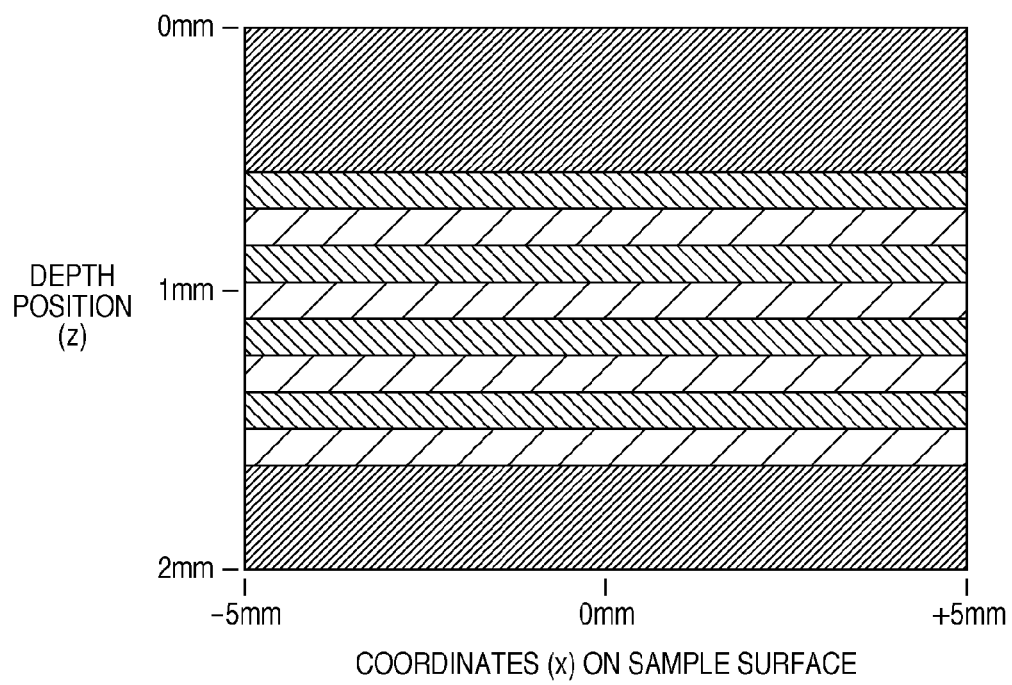
F I G. 11
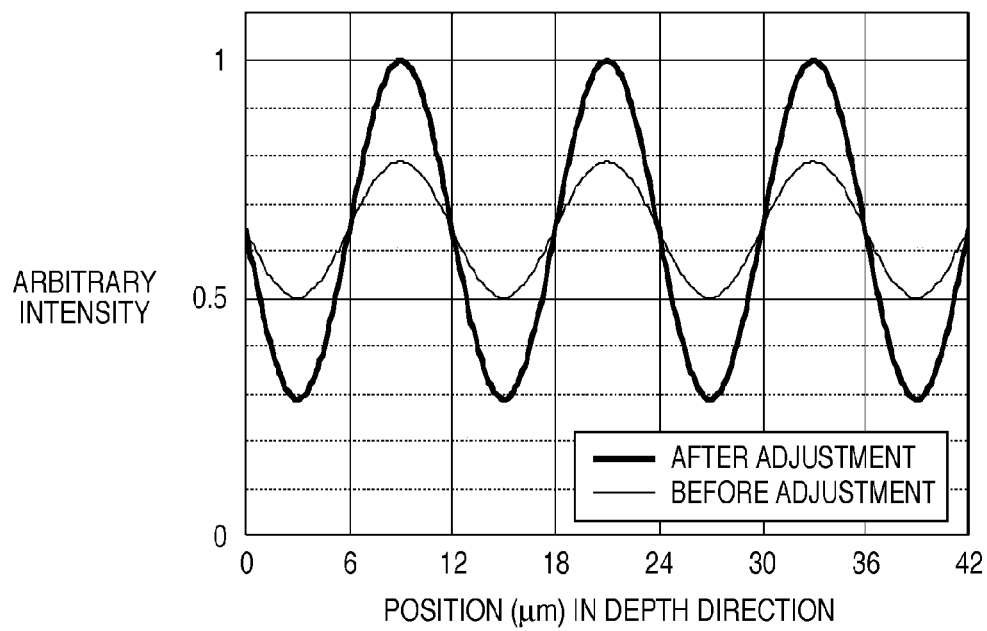

SCHEMATIC EYE AND ADJUSTMENT METHOD AND EVALUATION METHOD FOR OPTICAL COHERENCE TOMOGRAPHY APPARATUS

BACKGROUND OF THE INVENTION

1. Field of the Invention

The present invention relates to a schematic eye and an adjustment method and evaluation method for an optical coherence tomography apparatus.

2. Description of the Related Art

As an apparatus which noninvasively captures (obtains) a tomogram of a living tissue (for example, the eye's retina), an optical coherence tomography apparatus (to be sometimes referred to as an OCT hereinafter) is known.

The optical coherence tomography apparatus two-dimensionally scans a light beam over the retina via a deflector and measures the resultant reflected light and backscattered light with an interferometer. This procedure obtains a three-dimensional image including information in the depth (vertical) direction.

Conventionally, in order to improve the image quality of tomograms obtained by the OCT, efforts have been made to increase resolution (resolving power). The image quality (spatial resolving power) of a three-dimensional image is evaluated separately based on a horizontal resolving power representing the resolving power in a direction perpendicular to the optical-axis direction of a light beam irradiated from the OCT and a vertical resolving power representing the resolution in the optical-axis direction. For this reason, different techniques are used to evaluate the respective spatial resolving powers.

In an OCT and SLO (Scanning Laser Ophthalmoscope), the designed horizontal resolving power of an image of the fundus is determined by the diameter of a beam spot scanned over the retina. In a fundus camera, the designed horizontal resolving power is determined by the NA of an optical system.

Such evaluation of a designed horizontal resolving power generally uses a schematic eye. A schematic eye includes a single lens or a plurality of lenses and is provided with a resolution chart at a surface corresponding to the retina. In an apparatus as a target of evaluation of a horizontal resolving power, this technique captures an image of this pattern and calculates the density (intensity) contrast of the pattern corresponding to each spatial frequency. This procedure evaluates the evaluation target apparatus to determine whether it has achieved a desired horizontal resolving power.

For example, in the schematic eye disclosed in Japanese Patent Laid-Open No. 2002-165759, a lens is disposed into the main body of the almost cylindrical schematic eye, and a resolution chart is arranged at a fundus conjugate position at the time of optometry by a fundus camera. This schematic eye has a reflecting member for light diffusion only on the rear side of the chart. The operator adjusts the focus on an eye to be examined while watching the monitor. The horizontal resolving power is evaluated in an in-focus state.

A vertical resolving power δ of an OCT is theoretically obtained as the half width of the coherence function of an interferometer. More specifically, this resolving power is calculated by $$\delta = 2 \cdot \ln(2) \cdot \lambda_0^2 / (\pi \cdot \Delta\lambda) \quad (1)$$

where $\lambda_0$ is the center wavelength of an irradiation light source and $\Delta\lambda$ is the half width of a wavelength spectrum.

OCTs generally use low-coherence light sources. However, in order to reduce the value of δ, a light source with a large value of $\Delta\lambda$ has been under development. Recently, it is reported that using a light source with $\Delta\lambda$ of 100 nm or more has achieved the vertical resolving power δ of about 3 μm.

These values are merely theoretical values, and hence it is desired to evaluate a vertical resolving power as well as a horizontal resolving power by measuring actual values. As described above, the evaluation of a vertical resolving power does not use any resolution chart like that used for the evaluation of a horizontal resolving power. As a technique of evaluating a vertical resolving power using actual values, there is known a technique of measuring a plant cell, a multilayer film, or the like whose approximate order of size is known. The technique disclosed in T. Ralston et. al., "Real-time interferometric synthetic aperture microscopy", Opt. Express (16) 2555-2569 (2008) forms a thin film by dispersing $TiO_2$ particles with an average particle size of 1 μm in silicon and evaluates the image quality of a tomogram based on the size of an image of each particle.

The value of δ (the vertical resolving power of the OCT) obtained by equation (1) given above is based on the premise that the wavelength-spectrum distribution of a light source has a Gaussian shape. FIG. 7A shows graphs respectively indicating a light-source spectrum distribution with a Gaussian shape and a corresponding coherence-function shape. In this case, $\Delta\lambda$ is 50 nm and derived δ is 6 μm.

In this case, for example, an SLD (Super Luminescent Diode) or the like is often used as a light source for the OCT. However, the spectrum distribution of an SLD often has a shape other than a Gaussian shape. FIG. 7B shows graphs respectively representing the spectrum distribution of an SLD and a corresponding coherence-function shape. In this case, the half width of the coherence function shown in the graph on the right side of FIG. 7B does not greatly differ from the value of δ obtained by equation (1), but the bottom portions of the curve greatly spread. That is, the sharpness decreases.

Although it depends on the specifications of an OCT, the sampling intervals in the vertical direction are practically limited to about several μm in many cases. For this reason, even evaluating a vertical resolving power by obtaining the width of a measured coherence function often fails to obtain the necessary accuracy.

A coherence function is the minimum unit in forming the vertical component of a tomogram, and corresponds to a point-image distribution function in an optical system, such as a camera, which forms two-dimensional images. Therefore, the vertical component of a tomogram distribution to be observed is obtained as the convolution between the actual scattering intensity distribution of an object to be examined and this coherence function.

The profiles of tomograms obtained by measuring a given object using OCTs respectively having the coherence functions shown in FIGS. 7A and 7B will be described below with reference to FIG. 8. In this case, the dotted line indicates an object having a rectangular periodic scattering-intensity distribution, the thin line indicates the profile of the tomogram obtained by measurement by the OCT having the coherence function in FIG. 7A, and the thick line indicates the profile of the tomograms obtained by measurement by the OCT having the coherence function in FIG. 7B.

As shown in FIG. 8, although the half widths of the coherence functions shown in FIGS. 7A and 7B are almost the same, the contrasts at positions in the images which correspond to high-frequency light greatly differ from each other, and the contrasts at low-depth positions (that is, shallow positions) decrease in difference. Therefore, δ (the half width of a coherence function) used as an index indicating a vertical resolving power is not necessarily appropriate as a value expressing a vertical resolving power when tomograms are visualized.

SUMMARY OF THE INVENTION

The present invention provides a technique of obtaining information for evaluating a resolving power in the optical-axis direction of light emerging from the optical system in an optical coherence tomography apparatus.

According to a first aspect of the present invention there is provided a schematic eye used for evaluation of an optical system in an optical coherence tomography apparatus which captures a tomogram of a fundus, the eye comprising: a first optical member which irradiated light from the optical system strikes; and a second optical member which irradiated light from the first optical member strikes, wherein a plurality of layers having different scattering intensities are formed on the second optical member in an incident direction of the irradiated light.

According to a second aspect of the present invention there is provided an evaluation method for an optical system in an optical coherence tomography apparatus which captures a tomogram of a fundus, the method comprising obtaining a tomogram of a plurality of layers formed on the above described schematic eye and evaluating a resolving power in a tomographic direction by using image information obtained from the tomogram.

According to a third aspect of the present invention there is provided an adjustment method for an optical coherence tomography apparatus, the method comprising: irradiating the above described schematic eye with measurement light via an optical system; obtaining scattering-intensity information obtained from the schematic eye by the irradiation; and adjusting the optical system based on the scattering-intensity information.

Further features of the present invention will be apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 3 is a graph showing an example of the luminance profile of a tomogram;

FIG. 10 is a view showing an example of a tomogram of the schematic eye 100 shown in FIG. 1; and FIG. 11 is a view for explaining the process of adjusting the thickness of a dispersion compensating glass 6.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

An example of the sectional arrangement of a schematic eye 100 according to this embodiment will be described first with reference to FIG. 1.

The schematic eye 100 is used for the evaluation of the optical system of an OCT (Optical Coherence Tomography apparatus) which captures a tomogram of the fundus. More specifically, the schematic eye is used to evaluate the resolution (vertical resolving power) of the optical system of the OCT along the optical-axis direction of light emerging from the OCT.

The luminance of an image captured by the OCT corresponds to the intensity of reflection/backscattering inside an object (eye to be examined). It is necessary to make the interior of the object (eye to be examined) have a proper scattering density at a predetermined position along the optical-axis direction so as to make the captured image have brightness.

In this embodiment, to make this density regularly change in a given pattern along the optical-axis direction of light, layers having different scattering intensities are formed along the optical-axis direction of light. This makes it possible to evaluate a vertical resolving power (the resolving power in the optical-axis direction) by providing an arrangement equivalent to a resolution chart used for the evaluation of a horizontal resolving power (the resolving power in a direction perpendicular to the optical-axis direction) in this embodiment.

Figure 1:
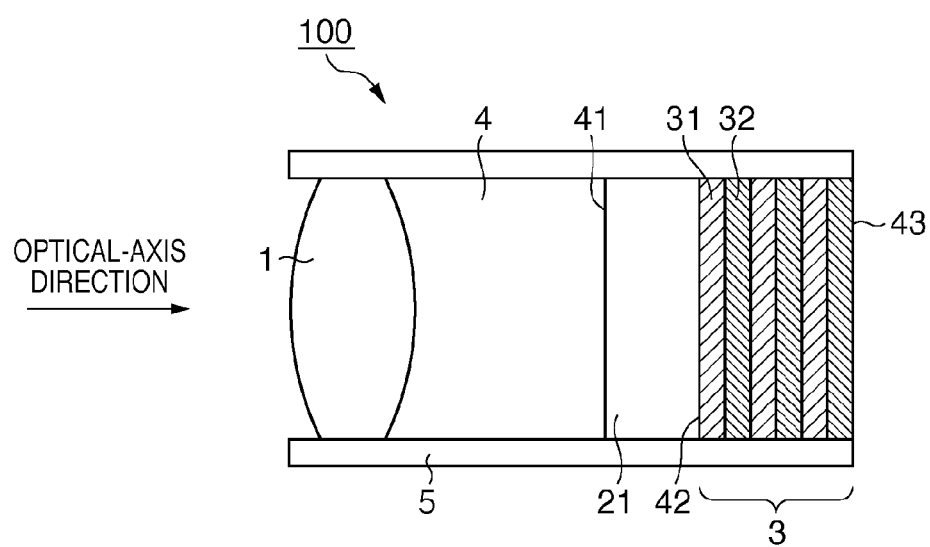
FIG. 1 is a view showing an example of the sectional arrangement of a schematic eye 100 according to an embodiment.

Referring to FIG. 1, the schematic eye 100 includes a lens 1, a glass substrate 21, a plurality of layers 3, and a cylindrical housing 5 which holds them. An area 4 between the lens 1 and the glass substrate 21 is filled with, for example, air. Note that this area may be filled with a liquid such as water or may be formed by a transparent solid such as glass.

With regard to the correspondence relationship between the schematic eye 100 and the (actual) eyeball, the lens 1 corresponds to the cornea and the crystalline lens, the area 4 and the glass substrate 21 correspond to the glass body, and the plurality of layers 3 correspond to the retina. For the sake of descriptive convenience, FIG. 1 shows the plurality of layers 3 larger than actual thickness.

The schematic eye 100 includes the lens 1 as the first optical member and the glass substrate 21 as the second optical member. Irradiated light strikes the lens 1 via the optical system of the OCT. Irradiated light from the optical system of the OCT strikes the glass substrate 21 via the lens 1.

The plurality of layers 3 are stacked on the glass substrate 21 in a direction opposite to the incident side of irradiated light. The glass substrate 21 is configured to make irradiated light sequentially strike it. The plurality of layers 3 have a plurality of first and second scattering layers 31 and 32 which are alternately formed. The first scattering layer 31 is formed from the first transparent medium (a medium having transparency), in which the first particles are dispersed at the first density. The second scattering layer 32 is formed from the second transparent medium, in which the second particles are dispersed at the second density.

Note that the first and second transparent media have, for example, a transmittance of 90% or more with respect to a light source wavelength $\lambda_c$ of the OCT. In this case, particles (first and second particles) having a refractive index different from that of a photo-curing material, such as an ultraviolet curable resin, are dispersed in the material. The resultant structure is formed into a thin film and cured. This forms the first and second transparent media. Note that it is possible to use a dispersant to prevent particles from aggregation or deposition.

The particle size of particles (first and second particles) is preferably equivalent to the center wavelength $\lambda_c$ of the light source used by the OCT or larger than $\lambda_c$ and smaller than a thickness t of the scattering layer. This is because, if the particle size is much smaller than the center wavelength $\lambda_c$ of the light source, scattering does not occur with a desired intensity, whereas if the particle size is larger than the thickness t of the scattering layer, the boundaries between the layers do not become uniform flat surfaces (or curved surfaces).

A material for particles (first and second particles) includes, for example, latex or silica particles. It is possible to use such a material as long as it has a refractive index different from that of transparent media (first and second transparent media).

Note that the first and second particles may have the same particle size and the same material quality (refractive index) or may have different particle sizes and different material qualities in accordance with, for example, the characteristics of cells of the respective layers of the actual fundus. If the two kinds of particles have the same material quality, for example, the particle size of the first particles is made larger than that of the second particles to let the two kinds of particles have different scattering intensities. In addition, if the two kinds of particles have the same particle size, for example, the number (or density) of first particles is made larger than that of the second particles to have different scattering intensities in the respective layers.

It is not always necessary to disperse particles in the first and second scattering layers 31 and 32. The first and second scattering layers 31 and 32 may be formed from a single material. The first and second scattering layers 31 and 32 may be formed by, for example, including fine spherical air bubbles in a single transparent material or may be formed by a porous material.

If the density of the particles in the first and second scattering layers 31 and 32 is too low, the S/N of a captured image decreases. If the density is too high, the degree of penetration of irradiated light decreases. Since the signal intensity of a captured image depends on the particle size, it is preferable to adjust the density to make the signal intensity equal to that of an image obtained when the actual fundus is observed.

In this case, the density of the first scattering layer 31 is adjusted to make the signal intensity of an obtained image almost equal to that obtained when the pigment epithelial layer of the fundus is observed. The density of the second scattering layer 32 is adjusted to make the signal intensity almost equal to that when the inner plexiform layer is observed. In addition, in order to evaluate the resolution when the contrast is highest, the particle density of the second scattering layer 32 may be set to 0 to make the layer transparent.

If the reflectance at the boundary surface between the respective layers is high, an area around the boundary may not be properly imaged because of the excessively high intensity of reflected light from the boundary surface. It is therefore preferable to use the same material for the first and second transparent media to prevent reflection at the boundary surface due to the refractive index difference between the two media.

When different materials are used for the first and second particles, it is possible to use different transparent media in accordance with the difference between the molecular structures of the materials to properly disperse the particles in the transparent media. In this case, in order to minimize the reflectance at the boundary surface, it is necessary to select media to minimize the difference between a refractive index $n_1$ of the first transparent medium (first scattering layer) and a refractive index $n_2$ of the second transparent medium (second scattering layer).

The same applies to a boundary surface 42 between the glass substrate 21 (refractive index $n_3$) and the plurality of layers 3. As described above, when the density of particles is set to make the intensity of a signal from the scattering layer almost equal to that of a signal from the fundus, the value of (scattered light intensity)/(irradiated light intensity) is about $10^{-5}$. The reflectance at each boundary surface is preferably lower than this value.

In this case, it is possible to select a material for the glass substrate 21, the transparent medium of the first scattering layer 31, and the transparent medium of the second scattering layer 32 so as to satisfy $$\{(n_j-n_k)/(n_j+n_k)\}^2 \leq 0.00001$$

for j, k=1 to 3, j≠k.

This makes it possible to reduce the influence of light regularly reflected by each boundary surface on an image. In addition, it is possible to obtain a proper image with few unnecessary components which is formed by only backscattered light from each scattering layer.

In order to evaluate the maximum vertical resolving power of the optical system of the OCT, it is necessary to obtain a spatial frequency corresponding to the half width $\delta$ (μm) of the coherence function ideally obtained from at least the half width of a light source spectrum. For this reason, the first and second scattering layers 31 and 32 of the schematic eye 100 include layers having thicknesses equal to or smaller than $\delta$ (μm). Note that in order to improve the measurement accuracy, it is preferable to set a layer thickness smaller than $\delta/2$ (μm).

When, for example, the operator wants to only grasp whether an image is resolved at $\delta$ (μm), the thickness of each of the first and second scattering layers 31 and 32 may be set to $\delta$ (μm). When the operator wants to evaluate a vertical resolving power for each spatial frequency, the first and second scattering layers 31 and 32 may respectively have different thicknesses.

Figure 9:
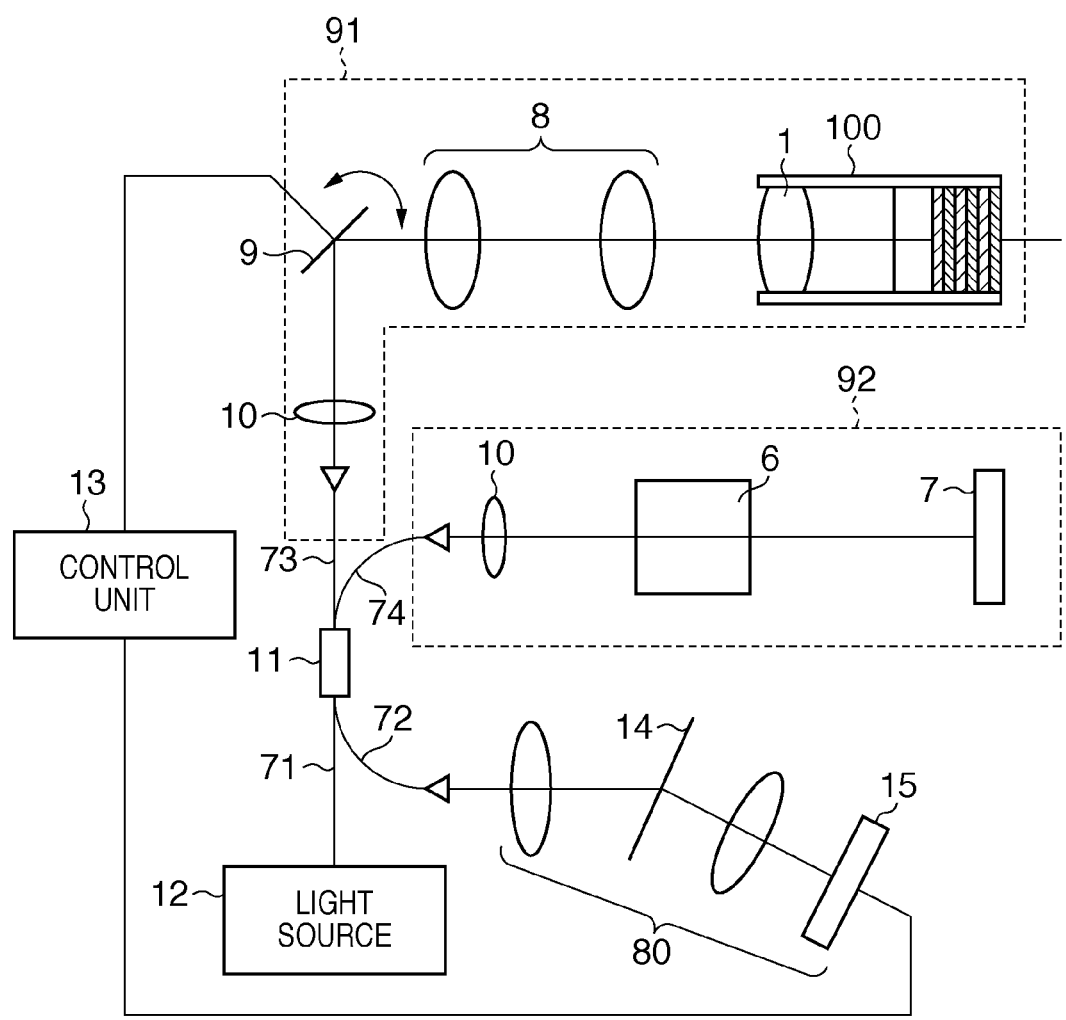
FIG. 9 is a view showing an example of the arrangement of the optical system of an OCT.

A technique of evaluating an OCT using the schematic eye 100 in FIG. 1 will be described below. FIG. 9 is a view showing an example of the arrangement of the optical system of the OCT.

In order to form a tomogram according to the principle of a low-coherence interferometer, the OCT includes an observation optical system 91 including an object to be examined and a reference optical system 92. The optical path length of the observation optical system 91 needs to be almost equal to that of the reference optical system 92. The two optical systems need to have nearly the same total dispersion value, that is, $\Sigma[-\lambda \cdot \{d^2 n_k(\lambda)/d\lambda^2\} \cdot d_k]$ (where $n_k$ is the refractive index of each portion including air, and $d_k$ is the spatial distance to each portion including air). If the two optical systems have different total dispersion values, the difference in the propagation velocity of light due to wavelengths will increase the coherence length, that is, the width of the coherence function, resulting in a decrease in vertical resolving power.

As a technique of compensating for such dispersion, there is known a technique of providing the reference optical system 92 with a dispersion compensating glass having dispersion equivalent to the value of dispersion caused in the observation optical system 91 including the eye. Since the dispersion value of an eyepiece optical system is known, a thickness $d_6$ of the dispersion compensating glass is also uniquely determined.

In this case, light (measurement light) from an SLD light source 12 propagates via a fiber 71 and strikes a coupler 11. The coupler 11 branches the incident light at a predetermined ratio to make one light component propagate to the observation optical system 91 via a fiber 73 and to make the other light component propagate to the reference optical system 92 via a fiber 74.

In the observation optical system 91, a light beam (beam) emerges from an end portion of the fiber 73. A collimator lens 10 collimates this beam. A scanner mirror 9 then deflects the beam in a two-dimensional direction. The deflected beam strikes the schematic eye 100 via an eyepiece lens 8. This beam is focused and scanned near the plurality of layers 3. Reflected light and backscattered light from each point of the plurality of layers 3 strike the fiber 73 via the lens 1, the eyepiece lens 8, the scanner mirror 9, and the collimator lens 10. In this case, since the thickness $d_6$ of a dispersion compensating glass 6 is determined on the premise that the human eye is arranged in the observation optical system 91, if the dispersion amount of the schematic eye 100 differs from that of the human eye, the coherence function spreads to decrease the vertical resolving power. This makes it impossible to properly evaluate the vertical resolving power. It is therefore preferable to design the schematic eye 100 so as to have the same dispersion amount as that of the human eye.

In the reference optical system 92, a light beam (beam) emerges from an end portion of the fiber 74. The collimator lens 10 collimates this beam, which is transmitted through the dispersion compensating glass 6 and strikes a return mirror 7. The return mirror 7 reflects the incident light toward the initial optical path. This causes the reflected light to strike the fiber 74 again via the same optical path as that of the incident light.

The coupler 11 multiplexes the respective light beams which have struck the fibers 73 and 74. The light (interference light) multiplexed by the coupler 11 propagates to a spectrometer 80 via the second imaging unit 72. A lens collimates the interference light which has struck the spectrometer 80. A grating 14 then demultiplexes the collimated light into light components of the respective wavelengths. The demultiplexed light components are formed into an image on a one-dimensional sensor 15 owing to the effect of an imaging lens.

The one-dimensional sensor 15 detects a light intensity corresponding to each wavelength to generate (convert it into) an electrical signal. The electrical signal is sent to a control unit 13. The control unit 13 converts the wavelength of the electrical signal into a wave number and then Fourier-transforms the signal to obtain a scattering intensity corresponding to the vertical position. Performing this operation at each position of a scanned light beam will obtain tomograms and a three-dimensional image.

Consider a case in which a center wavelength $\lambda_0$ of the light source 12 is 850 nm, and the half width $\Delta\lambda$ of a wavelength spectrum is 50 nm. In this case, the half width $\delta$ of the coherence function obtained by calculation is about 6 μm. For this reason, each of the plurality of layers 3 of the schematic eye 100 is formed to have a thickness of 6 μm.

In this case, the first scattering layer 31 is dispersed with particles at a predetermined density, and the second scattering layer 32 is formed as a transparent layer with a particle density of 0. For example, the image shown in FIG. 10 is obtained as a tomogram of this schematic eye. In this case, scattering-intensity information corresponding to a position in the depth direction (z) in scattering layer plane direction x=0 is obtained, and its luminance profile is displayed on a display, as shown in FIG. 3. That is, the display displays the relationship between position information in the depth direction and the scattering-intensity information.

In this case, simultaneously displaying the luminance contrast value $$\Delta D = (D\max - D\min)/(D\max + D\min)$$

allows the evaluation of the resolution in the tomographic direction. Note that when scattering layers are formed on planes as shown in FIG. 1, since the incident angles of irradiated beams differ depending on positions (x) in the plane direction, optical paths passing through the respective scattering layers differ from each other. In this case, therefore, it is necessary to correct coordinates (z) in the depth direction in FIG. 3.

It is possible to directly evaluate the vertical resolving power of the OCT as an evaluation target from the image information obtained in this manner.

As described above, the dispersion in the observation optical system 91 is ideally uniform, and the thickness $d_6$ of the dispersion compensating glass 6 is uniquely determined. In practice, however, manufacturing errors and the like occur, and hence it is necessary to adjust the thickness $d_6$ so as to optimize the vertical resolving power. A procedure for finely adjusting $d_6$ by using the schematic eye 100 of this embodiment will be described with reference to the arrangement shown in FIG. 2.

If the dispersion compensating glass 6 does not have an appropriate thickness in the optical-axis direction, the coherence function spreads to decrease the vertical resolving power. For this reason, the dispersion compensating glass 6 is adjusted according to the following procedure.

Figure 2:
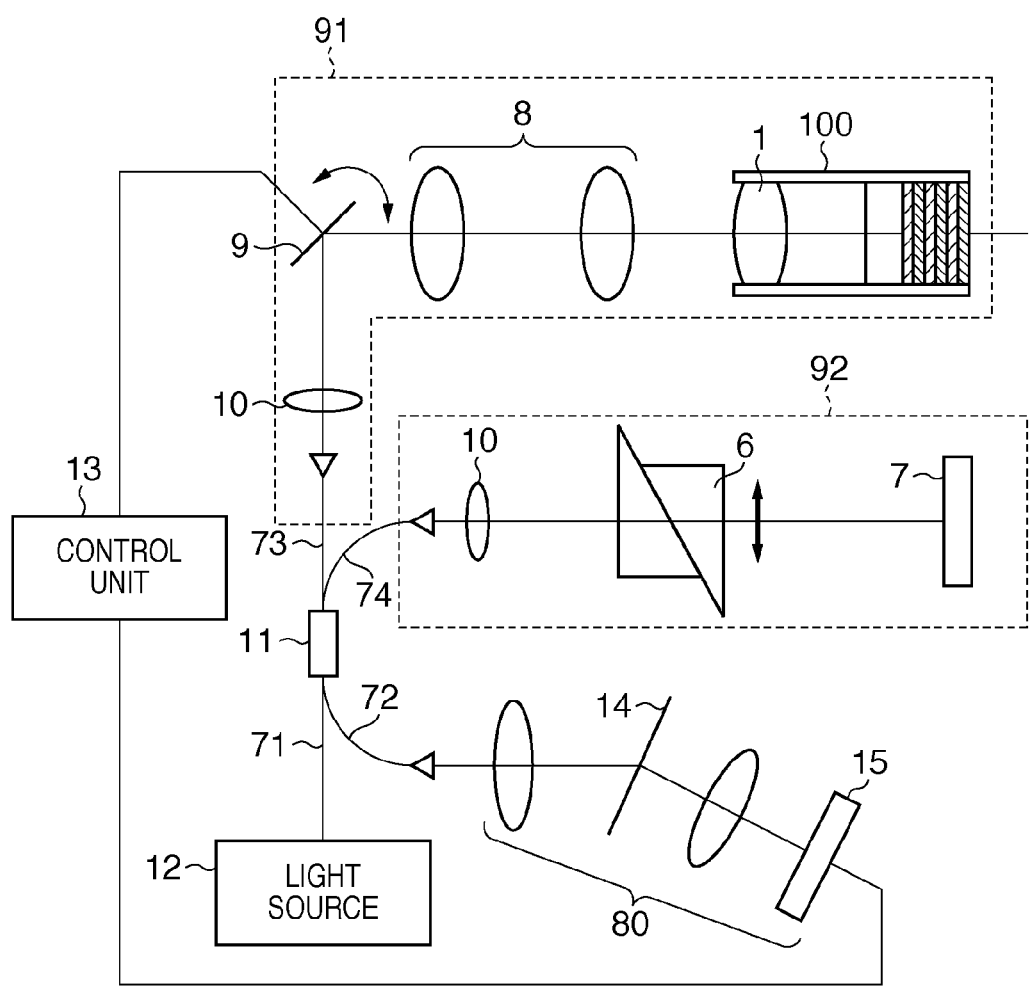
FIG. 2 is a view showing an example of the arrangement of the optical system of an OCT.

First of all, the thickness $d_6$ of the dispersion compensating glass 6 is set to a predetermined value based on the design dispersion value of the apparatus. The arrangement in FIG. 2 is basically the same as that shown in FIG. 9 but differs from it in that the dispersion compensating glass 6 includes two wedge-shaped prisms with their inclined surfaces being in tight contact with each other. With this arrangement, the operator slides the prisms of the glass 6 relative to each other along the inclined surfaces by operating an operation unit (not shown). This allows arbitrarily adjusting of the thickness in the optical-axis direction. At this time, the schematic eye 100 is set at a position corresponding to the eye and is arranged to focus a beam at each position in the plurality of layers 3.

In this case, the luminance contrast value:

$$\Delta D = (D\max - D\min)/(D\max + D\min)$$

is also simultaneously displayed in real time. The operator refers to this value and adjusts the thickness of the dispersion compensating glass 6 so as to maximize the value. For example, FIG. 11 shows the adjustment process. Before the adjustment of the thickness $d_6$ of the glass 6, the intensity distribution of a profile at a given x position in the tomogram is displayed in real time as indicated by the thin line. In this case, the value of $\Delta D$ is about 0.23. This value is also displayed. Changing the value of $d_6$ so as to maximize the value of $\Delta D$ leads to a luminance-profile distribution indicated by the thick line. The value of $\Delta D$ is about 0.54. Note that the control unit 13 may automatically perform this adjustment.

As described above, the schematic eye according to the first embodiment has layers with different scattering intensities formed along the optical-axis direction (incident direction) of irradiated light from the OCT. This allows evaluating of the resolving power in the optical-axis direction in the OCT based on the information obtained by the OCT. In addition, this allows adjusting of the optical system of the OCT based on the evaluation. That is, it is possible to obtain information for evaluating the resolving power in the optical-axis direction of light emerging from the optical system of the OCT (optical coherence tomography apparatus).

Second Embodiment

The second embodiment will be described next. In the first embodiment, an end face 43 of the plurality of layers 3 is a boundary surface with the outside (air). The second embodiment will exemplify a case in which consideration is given to the reflectance of light at the end face 43.

Figure 4:
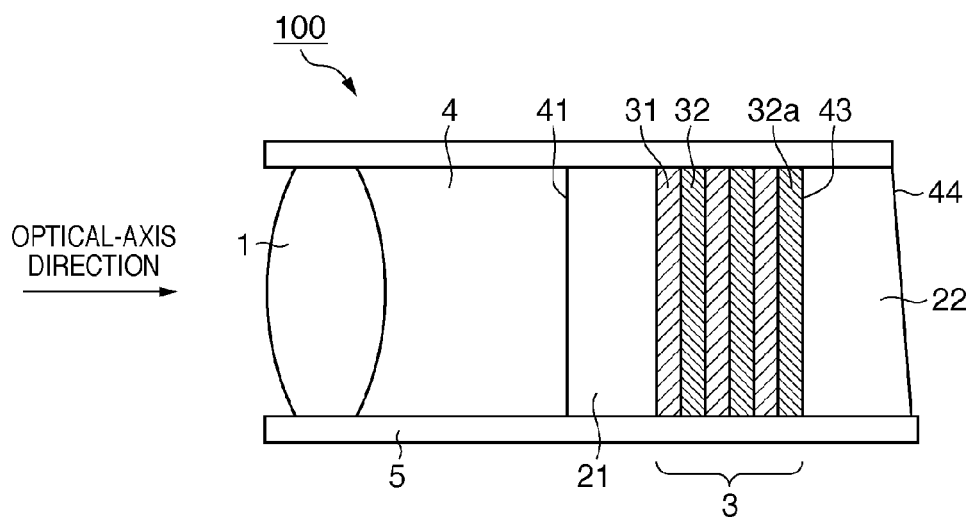
FIG. 4 is a view showing an example of the sectional arrangement of a schematic eye 100 according to the second embodiment.

FIG. 4 is a view showing an example of the sectional arrangement of a schematic eye 100 according to the second embodiment. The same reference numerals as in FIG. 1 in the first embodiment denote the same parts, and a description of them will be omitted.

The schematic eye 100 according to the second embodiment includes a glass substrate 22 in addition to the arrangement of the first embodiment. The glass substrate 22 is provided as a third optical member on the end face (the surface on the opposite side to the surface which irradiated light from the OCT strikes) 43 side of the plurality of layers 3. That is, the glass substrate 22 is provided at a position on a second scattering layer 32a which is far from the incident side. The glass substrate 22 is made of a material having the same refractive index as that of the transparent medium of a first scattering layer 31 or second scattering layer 32 or a material which slightly differs in refractive index from it. This structure and composition reduces the reflectance at the end face 43.

A boundary surface 44 (with the outside) at which the glass substrate 22 is in contact with the outside is a boundary surface with air. If the OCT is a confocal optical system, since the boundary surface 44 comes off the imaging surface as the thickness of the glass substrate 22 increases, it is possible to reduce reflected light from the boundary surface 44. The same applies to the setting of the thickness of the glass substrate 21 in relation to reflection at a boundary surface 41.

In addition, the glass substrate 22 is configured such that the boundary surface 44 tilts relative to the optical axis to prevent regularly reflected light from returning to the OCT side. Note that the boundary surface 44 may be formed by a predetermined curved surface. In addition, the glass substrate 22 may be formed by using the same material as that for the transparent medium of the first scattering layer 31 or second scattering layer 32. In this case, forming the glass substrate 22 to a thickness larger than those of these layers (first and second scattering layers 31 and 32) can suppress regularly reflected light from returning to the OCT side as in the above case.

As described above, the schematic eye according to the second embodiment has the glass substrate 22 having a predetermined thickness provided on the surface on the opposite side to the surface which irradiated light from the OCT strikes. This arrangement can suppress unnecessary reflected light from being included in a measurement result at the time of evaluation and adjustment, as in the first embodiment. This arrangement can evaluate the resolving power of the OCT in the optical-axis direction with higher accuracy than that in the arrangement of the first embodiment.

Third Embodiment

Figure 5:
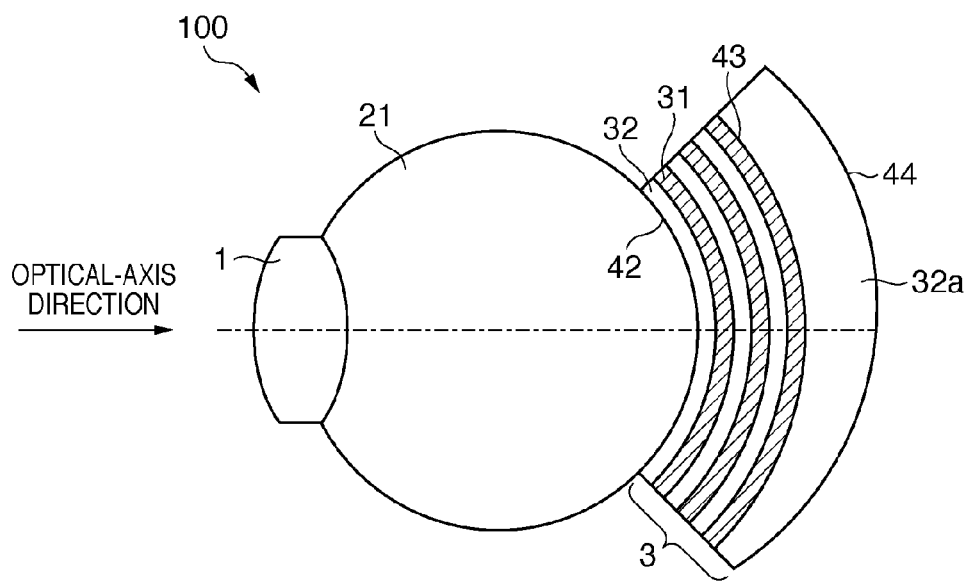
FIG. 5 is a view showing an example of the sectional arrangement of a schematic eye 100 according to the third embodiment.

The third embodiment will be described next. FIG. 5 is a view showing an example of the sectional arrangement of a schematic eye 100 according to the third embodiment.

The schematic eye 100 according to the third embodiment has a spherical surface formed on the opposite side to the incident side of a glass substrate 21 which irradiated light strikes, and is provided with a plurality of layers 3 behind the spherical surface. The plurality of layers 3 have first and second scattering layers 31 and 32 alternately stacked on each other. Each second scattering layer 32 is formed from a transparent layer with a particle density of 0.

Although the first scattering layers 31 and the second scattering layers (to be referred to as transparent layers hereinafter) 32 are formed to have a uniform thickness, a transparent layer 32a formed on the outermost side has a thickness larger than that of the remaining transparent layers 32. A boundary surface 44 of the transparent layer 32a is formed to have a spherical shape shifted relative to the optical axis. This arrangement prevents light regularly reflected by the boundary surface 44 from returning regardless of field angles at which the light beams strike.

In this case, the lens 1 and the glass substrate 21 constitute a compound lens. The focal length of this compound lens is designed to be, for example, 22.785 mm according to the specifications of a Gullstrand schematic eye. Light striking the center of the lens 1 is focused on a rear surface 42 of the glass substrate 21.

The material for the glass substrate 21 is glass having refractive index $n_3=1.491477$ at a wavelength of 840 nm. As a transparent medium used for each of the first scattering layers 31 and the transparent layers 32, for example, an ultraviolet curable resin having refractive index $n_1=1.49$ at a wavelength of 840 nm is used. In this case, the reflectance at the boundary surface 42 is $2.5 \times 10^{-5}$%.

Figure 6:
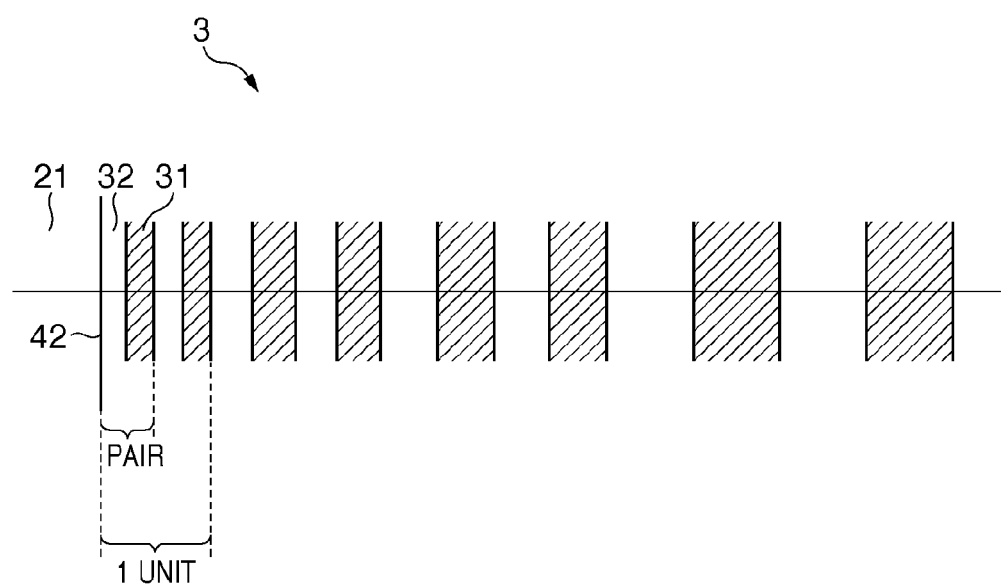
FIG. 6 is a view schematically showing an example of the arrangement of a plurality of layers 3 shown in FIG. 5.
Figure 7A:
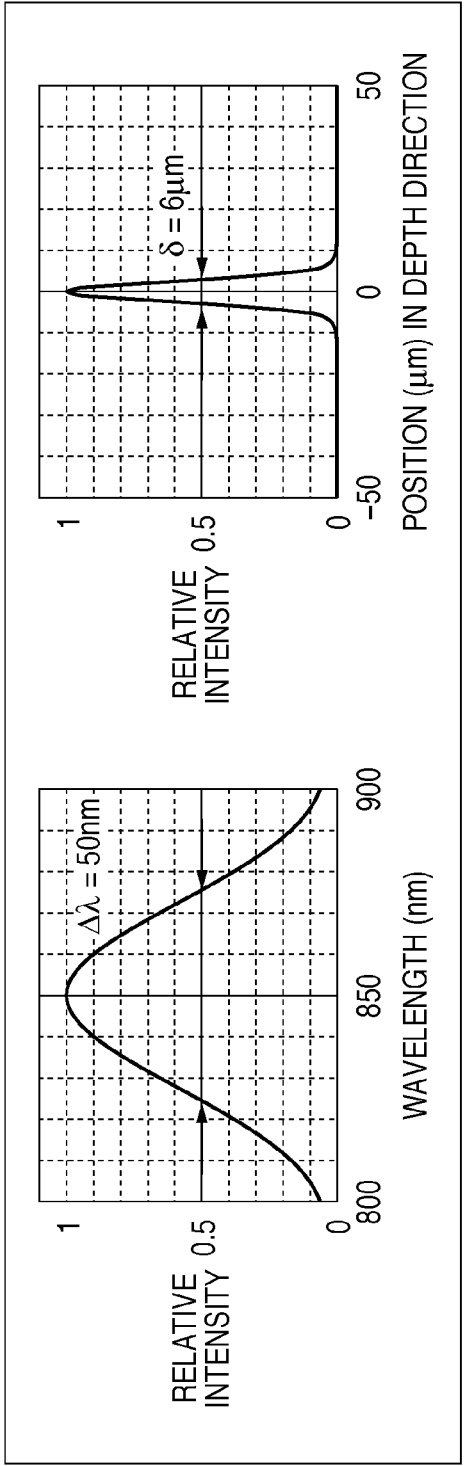
FIGS. 7A and 7B are graphs for explaining an example of the prior art.
Figure 7B:
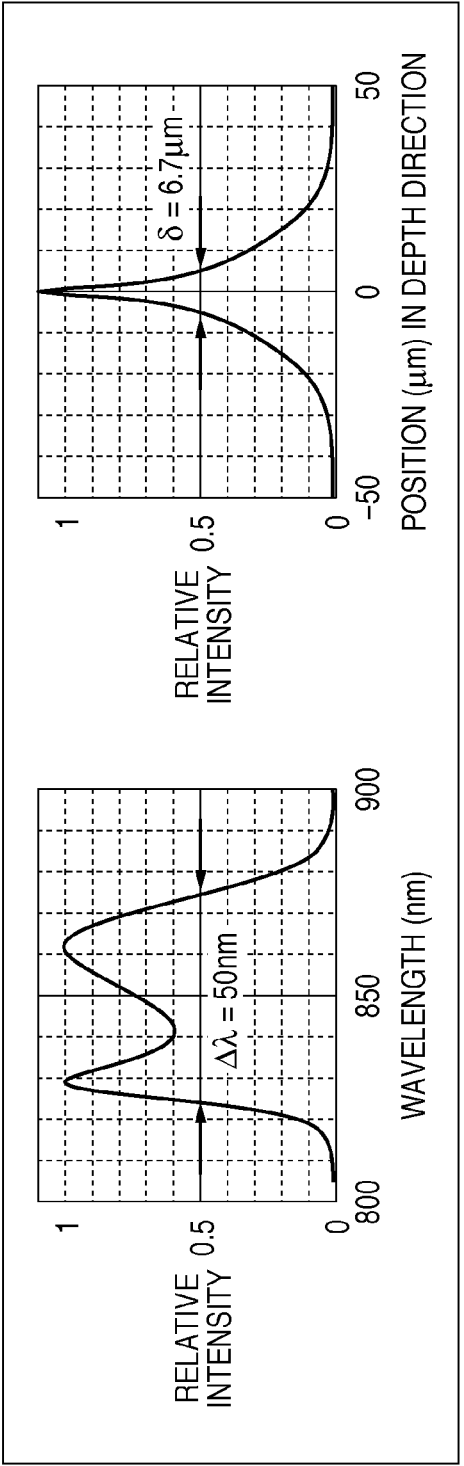
Figure 8:
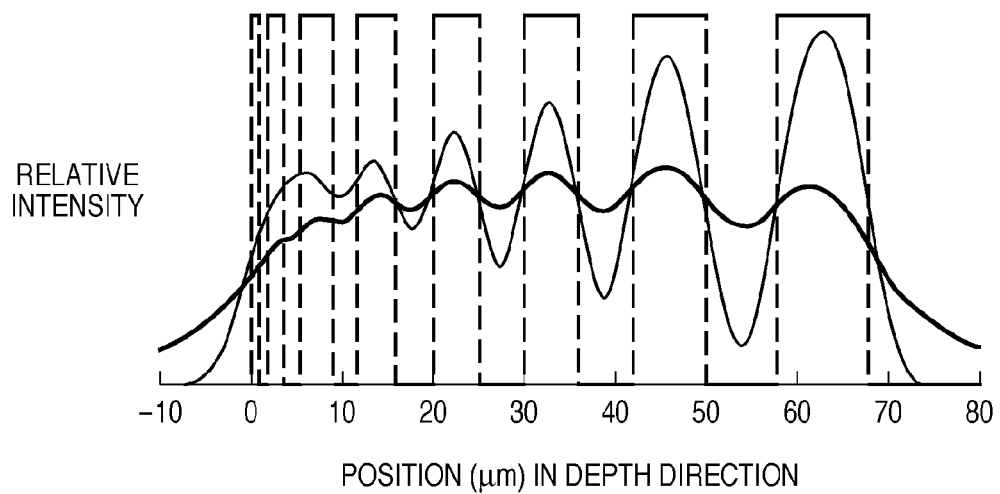
FIG. 8 is a graph for explaining an example of the prior art.

FIG. 6 is a view schematically showing an example of the arrangement of the plurality of layers 3 shown in FIG. 5.

As described above, the transparent layers 32 and the first scattering layers 31 are alternately formed on the boundary surface 42 of the glass substrate 21 in the order named. In this case, each transparent layer 32 and each first scattering layer 31 which are adjacent to each other constitute a pair. The respective layers constituting a pair have the same thickness. In the case shown in FIG. 6, two pairs constitute one unit, in which the respective layers have the same thickness. That is, the plurality of layers include a plurality of units having different layer thicknesses, which gradually increase along the optical-axis direction of light. This arrangement allows measuring of an intensity contrast for each spatial frequency. Note that each unit need not always be constituted by two pairs. Each unit may be formed by, for example, one pair or three pairs, and the layer thickness may be changed for each unit.

When an OCT in which a half width $\delta$ of the coherence function obtained by equation (1) is 6 μm is to be evaluated, the layer thickness of the respective units are 3 μm, 4.5 μm, 6 μm, and 9 μm when seen from the boundary surface 42.

Capturing a tomogram using the schematic eye 100 having the above arrangement allows calculating of a contrast value for each spatial frequency. This makes it possible to grasp up to which frequency the evaluated OCT can satisfactorily resolve.

Note that when a unit with a large layer thickness is arranged on the incident side, the amount of light reaching a unit with a small layer thickness which is arranged at a deep position in the optical-axis direction of light decreases. In addition, the intensity of return light (reflected light and backscattered light) also decreases.

According to an SD (Spectral-Domain) OCT like that described with reference to FIG. 3, the signal intensity decreases in principle toward deeper positions, depending on the number of pixels of a one-dimensional sensor 15 to be used. For this reason, in this embodiment, in order to suppress a deterioration in the measurement accuracy of contrast values at high frequencies, a unit with a small layer thickness is arranged on the incident side of irradiated light, that is, on the glass substrate 22 side.

Note that the schematic eye 100 according to the third embodiment allows the evaluation and adjustment of an OCT as in the first embodiment. In this case, since the layer corresponding to the fundus has the spherical surface, it is possible to perform a more realistic evaluation and adjustment for light to be two-dimensional scanned.

The typical embodiments of the present invention have been described above. However, the present invention is not limited to the embodiments described above and shown in the accompanying drawings, and can be modified and executed as needed within the spirit and scope of the invention.

Note that the arrangements according to the first to third embodiments may be partly combined. For example, the third embodiment may include the first and second scattering layers 31 and 32 having a predetermined density as the plurality of layers 3. In addition, it is possible to use the transparent layer described in the third embodiment in place of the glass substrate 22 covering the outer portion. It is also possible to use the glass substrate described in the second embodiment in place of the transparent layer described in the third embodiment. The same applies to, for example, the manner of setting layer thicknesses.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-092627 filed on Apr. 13, 2010, and No. 2011-044299 filed on Mar. 1, 2011, which are hereby incorporated by reference herein in their entirety.

What is claimed is:

1. A schematic eye used for evaluation of an optical system in an optical coherence tomography apparatus which captures a tomogram of a fundus, the eye comprising:
a first optical member which irradiated light from the optical system strikes and from which scattered light is emitted to the optical system;
a second optical member which irradiated light from said first optical member strikes; and
a plurality of layers having different scattering intensities formed on said second optical member in an incident direction of the irradiated light,
wherein the scattered light is light that is generated by said second optical member scattering the irradiated light.

2. The eye according to claim 1, wherein the plurality of layers comprise a plurality of first scattering layers formed by dispersing, in a medium having transparency, first particles having a refractive index different from that of the medium and a plurality of second scattering layers formed by dispersing, in a medium having transparency, second particles having a refractive index different from that of the medium and the first particles, said plurality of first scattering layers and said plurality of second scattering layers being alternately formed along an optical-axis direction of the irradiated light.

3. The eye according to claim 2, wherein the first particles and the second particles have a particle size equal to a center wavelength of the irradiated light, or larger than the center wavelength and smaller than a thickness of the first scattering layer and second scattering layer in the optical-axis direction.

4. The eye according to claim 2, wherein the first particles or the second particles have a density of 0.

5. The eye according to claim 2, wherein a refractive index $n_1$ of said second optical member, a refractive index $n_2$ of the first scattering layer, and a refractive index $n_3$ of the second scattering layer satisfy $$\{(n_j-n_k)/(n_j+n_k)\}^2 \leq 0.00001, \text{ where}$$

(j, k=1 to 3, j≠k).

6. The eye according to claim 2, wherein the first scattering layer and the second scattering layer which are adjacent to each other constitute a pair,
wherein the first and second scattering layers comprising the pair have the same thickness in the optical-axis direction, and
wherein the plurality of layers are formed such that the thickness thereof changes along the optical-axis direction for each unit of layers including the pair or a plurality of pairs of adjacent first and second scattering layers.

7. The eye according to claim 1, wherein the plurality of layers comprise a plurality of first scattering layers formed by dispersing, in a medium having transparency, first particles having a refractive index different from that of the medium and a plurality of second scattering layers formed by dispersing, in a medium having transparency, second particles made of the same material as that of the first particles, said plurality of the first scattering layers and said plurality of the second scattering layers being alternately formed along an optical-axis direction of the irradiated light, and the first particles in the first scattering layer and the second particles in the second scattering layer having different particle sizes or different densities.

8. The eye according to claim 1, wherein a surface of said second optical member, which is located on a side of said second optical member opposite to an incident side of said second optical member on which the irradiated light is incident, is formed by a spherical surface, and wherein the plurality of layers are stacked on each other in a shape covering part of the spherical surface.

9. The eye according to claim 1, wherein a layer, of the plurality of layers, which is provided on an end portion of said second optical member on an opposite side of said second optical member from the incident side of said second optical member on which the irradiated light is incident along the optical-axis direction of the irradiated light, is thicker than other layers in the optical-axis direction.

10. The eye according to claim 1, further comprising a third optical member provided on a layer, of the plurality of layers, which is provided on an end portion of said second optical member on an opposite side of said second optical member from the incident side of said second optical member on which the irradiated light is incident along the optical-axis direction of the irradiated light.

11. An evaluation method for an optical system in an optical coherence tomography apparatus which captures a tomogram of a fundus, the method comprising the steps of:

obtaining a tomogram of a plurality of layers formed on a schematic eye used for evaluation of an optical system in the optical coherence tomography apparatus which captures a tomogram of a fundus, the eye comprising a first optical member which irradiated light from the optical system strikes and from which scattered light is emitted to the optical system, a second optical member which irradiated light from said first optical member strikes, and a plurality of layers having different scattering intensities formed on said second optical member in an incident direction of the irradiated light, wherein the scattered light is light that is generated by said second optical member scattering the irradiated light; and evaluating a resolving power in a tomographic direction by using image information obtained from the tomogram.

12. An adjustment method for an optical coherence tomography apparatus, the method comprising the steps of:

irradiating a schematic eye with measurement light via an optical system, the schematic eye being used for evaluation of an optical system in the optical coherence tomography apparatus which captures a tomogram of a fundus, the eye comprising a first optical member which irradiated light from the optical system strikes and from which scattered light is emitted to the optical system, a second optical member which irradiated light from said first optical member strikes, and a plurality of layers having different scattering intensities formed on said second optical member in an incident direction of the irradiated light, wherein the scattered light is light that is generated by said second optical member scattering the irradiated light;

obtaining scattering intensity information obtained from the schematic eye by the irradiation; and adjusting the optical system based on the scattering intensity information.

13. The method according to claim 12, further comprising the step of displaying a relationship between the obtained scattering intensity information and position information in a depth direction.

* * * * *